United States Patent [19]

Ali

[11] Patent Number: 4,717,715
[45] Date of Patent: Jan. 5, 1988

[54] ARG[7]-ARG[8]-VASOPRESSIN ANTAGONISTS
[75] Inventor: Fadia E. Ali, Cherry Hill, N.J.
[73] Assignee: SmithKline Beckman Corporation, Philadelphia, Pa.
[21] Appl. No.: 877,571
[22] Filed: Jun. 23, 1986
[51] Int. Cl.$^4$ .................... H61K 37/34; C07K 7/16
[52] U.S. Cl. ........................ 514/11; 514/807; 530/315
[58] Field of Search ............... 514/11, 807; 530/315
[56] References Cited
U.S. PATENT DOCUMENTS 4,469,679  9/1984  Huffman et al. ............ 530/315
4,481,193  11/1984  Ali et al. .................... 530/315
4,481,194  11/1984  Ali et al. .................... 530/315

OTHER PUBLICATIONS

M. Manning et al., Nature, 308 652 (1984).

Primary Examiner—Delbert R. Phillips
Attorney, Agent, or Firm—Janice E. Williams; Stuart R. Suter; Alan D. Lourie

[57] ABSTRACT

Vasopressin antagonists which have a dipeptide side chain comprised of two basic amino acids demonstrate potent $V_1$ and $V_2$-antagonist activity. A species of the invention, which is prepared by conventional peptide sequencing, is [1-($\beta$-mercapto-$\beta$,$\beta$-cyclopentamethylene propionic acid)-2-(O-ethyl)-D-tyrosine-4-valine-7-arginine-8-arginine-9-desglycine]-vasopressin.

16 Claims, No Drawings

ARG⁷-ARG⁸-VASOPRESSIN ANTAGONISTS

This invention relates to certain new cyclic octapeptides which have potent vasopressin antagonist activity. The structures of these octapeptides are distinguished by having a dipeptide tail which is comprised of two basic amino acid units and which is directly attached to the cysteine unit of a vasopressin-like ring.

BACKGROUND OF THE INVENTION

M. Manning et al., Nature, 308 652 (1984) and U.S. Pat. No. 4,469,679 have disclosed that the terminal glycine unit at the 9-position of certain vasopressin-like antagonists can be removed or replaced by L or D-Ala, Ser or Arg without necessarily affecting binding at vasopressin receptors.

U.S. Pat. Nos. 4,481,194 and 4,481,193 discloses that either removing proline at position 7 or both proline and glycine at positions 7 and 9 from the structures of vasopressin antagonists gives compounds which retain substantial, but somewhat reduced, antagonist activity.

The vasopressin-like compounds of this invention have structures which are distinguished over the prior art in that two basic amino acid units, such a arginine or lysine, are attached directly to the disulfide VSP ring. The compounds are very potent vasopressin antagonists.

In the description herein and in the claims, the nomenclature common in the art of peptide and vasopressin chemistry is used. When no configuration is noted, the amino acid unit is in the L, or naturally occurring, form. In certain structural formulas, the thio members of the Cap, Mpa and Cys units are added for clarity.

Certain of the peptide art designations used herein are the following: Cap, β-mercapto-β,β-cycloalkylenepropionic acid; Pmp, β-mercapto-β,β-cyclopentamethylenepropionic acid; Mpr, β-mercaptopropionic acid; dPen, β-mercapto-β,β-dimethylpropionic acid or desaminopenicillamine; Tyr (Alk), O-alkyltyrosine; Abu, α-amino-n-butyric acid; Chg, cyclohexylglycine; Cha, cyclohexylalanine; Pba, α-aminophenylbutyric acid; Gln, glutamic acid amide or glutamine; Gly, glycine; Tyr, tyrosine; Phe, phenylalanine; Phe (4'-Alk), 4'-alkylphenylalanine; MeAla, N-methylalanine; Val, valine; Ile, isoleucine; Nle, norleucine; Leu, leucine; Ala, alanine; Lys, lysine; Arg, arginine; HArg, homoarginine; MeArg, N-methylarginine; MeHArg, N-methylhomoarginine; MeLys, N-methyllysine; Met, methionine; Asn, asparagine; Sar, sarcosine; Tos, tosylate; BHA, benzhydrylamine; DMAP, 4-dimethylaminopyridine; DIEA, diisopropylethylamine; HF, hydrogen fluoride; 4-MeBzl, 4-methylbenzyl; TFA, trifluoroacetic acid; DCC, dicyclohexylcarbodiimide; Boc, t-butyloxycarbonyl; Z, benzyloxycarbonyl; VSP, vasopressin; HBT, hydroxybenzotriazole; ACM, acetamidomethyl; Mpa, noncyclic β-mercaptopropionic acids. In the definitions such as MeArg above, Me denotes a methyl located on the amido nitrogen of the peptide unit concerned.

"Alk" represents a lower alkyl of 1–4 carbons. For example, these may be optionally attached to the oxygen substituent of a tyrosine unit at position 2, to the N-terminal nitrogen of the tail, or to the 4'-position of a Phe unit at position 3. Such alkyl substituents include methyl, ethyl, n-propyl, isopropyl or butyl. Ethyl is preferred. When the term, "vasopressin", is used, it means L-arginine vasopressin (AVP) unless otherwise modified. The 1-(β-mercaptocycloalkylene)propionic acid unit (Cap) at position 1 is often referred herein as Pmp for convenience since the pentamethylene containing unit is preferred. All the β-mercaptopropionic acids may be, at times, referred to herein as Mpr.

DESCRIPTION OF THE INVENTION

The basic vasopressin antagonist compounds of this invention are illustrated by the following structural formula:

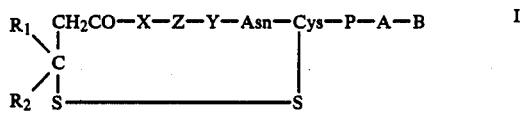

in which:
P is a D or L isomer of Arg, Lys, HArg, MeArg, MeLys or MeHArg;
A is a D or L isomer of Arg, Lys, HArg, MeArg, MeLys or MeHArg;
B is OH, NH₂ or NHAlk;
Z is Phe, Phe(4'-Alk), Tyr(Alk), Ile or Tyr;
X is a D or L isomer of Phe, Phe(4'-Alk), Val, Nva, Leu, Ile, Pba, Nle, Cha, Abu, Met, Chg, Tyr or Tyr(Alk);
Y is Val, Ile, Abu, Ala, Chg, Gln, Lys, Cha, Nle, Thr, Phe, Leu or Gly; and
R₁ and R₂ are, each, hydrogen, methyl or, when taken together, a cycloalkylene ring of 4–6 members taken with the β-carbon to which they are attached.

A subgeneric group of compounds of this invention comprises compounds of formula I in which P is Arg, A is Arg and B is NH₂. In formula I, R₁ and R₂ are, preferably, cyclopentamethylene.

Also included in this invention are addition salts, complexes or prodrugs such as esters of the compounds of this invention when B is OH, especially the nontoxic, pharmaceutically acceptable acid addition salts. The acid addition salts are prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. The end products of formula I have two strong basic groups in their structures, therefore, their acid addition salt derivatives are easily prepared. The ester derivatives of the acid forms of the end products, such as the methyl, ehtyl or benzyl esters, are prepared as known to the art.

The end products (I) of this invention are prepared by oxidation of the following linear heptapeptide:

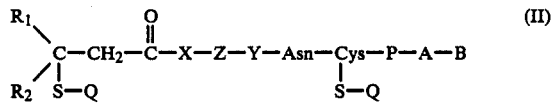

in which X, Z, Y, P, A, B, R₁ and R₂ are as defined for formula I above. The mercapto groups are members of the units at positions 1 and 6. Each Q is hydrogen or a displaceable protective group such as acetamidomethyl (ACM). The dithiol of formula II may be also oxidized in the form of an ester or amide derivative of the unit at position 8. For example, the amide may be those peptides of Formula II in which B is —NHAlk or —NH₂. The esters would have B as OAlk or OBzl.

Said oxidation is carried out using an excess of an alkali metal ferricyanide, such as potassium or sodium ferricyanide, with the linear intermediate II. A suitable unreactive solvent, preferably an aqueous-miscible solvent at a neutral pH, about 7-7.5, is used. Reaction is carried out at ambient temperature or lower until the reaction is substantially complete. Preferably, the concentrations of the linear peptide dimercaptan and the oxidizing agent are low, say 0.01-0.1 molar concentration of oxidizing agent in several liters of aqueous solution to cyclize 1-5 grams of dimercaptan.

Other mild oxidation agents having an oxidation potential roughly equivalent to ferricyanide may also be used for the ring closure reaction. Oxygen passage through the reaction solution for several days, iodine in methanol, hydrogen peroxide or oxidation in the presence of cupric salts are such alternatives. Cyclization, also, occurs when a displaceable, thiol-protective group such as that at the mercaptan group of the Pmp unit is displaced intramolecularly.

An especially useful thio protective group is acetamidomethyl (ACM). Iodine/alcohol is used for direct, one-pot cyclization of the bis-ACM-S linear peptide.

Of course, one skilled in the art will recognize that certain cyclization methods are not appropriate if an interfering reaction site is present in the structure of the starting material of formula II. The linear mercaptan starting material may have common protective groups temporarily present at the various linear units.

The peptide chain of the linear peptides is usually built up, stepwise, proceeding from the A unit and working toward the Mpa or Pmp unit. Each unit is properly protected as known in the peptide art and as described below. The sequence of step-reactions is conveniently carried out in a Beckman 990B peptide synthesizer or its equivalent without isolation of each intermediate peptide. The details of the procedure are in the working examples presented hereinafter.

The various amino acids (AA), which are consecutively added to the resin-supported chain, are protected as known to the art. For example, the Boc protecting group is used for an amino group, especially at the α-position; an optionally substituted benzyl, for the mercapto groups at the Pmp, Mpa or Cys units; tosyl for the Arg, HArg or MeArg unit; and an optionally substituted carbobenzyloxy (Z) for the Tyr or Lys units. The protective groups are, most conveniently, those which are not easily removed by using mild acid treatment, such as for removing the Boc group. Rather one should use HF, sodium-liquid ammonia or, for benzyl or carbobenzyloxy groups, catalytic hydrogenation.

The resin supported peptide is treated with an excess of anhydrous hydrogen fluoride with an appropriate scavenger compound, such as anisole, to give the linear peptide intermediate of formula II in good yield.

The compounds of formula I are also prepared by reacting the Arg acid with a protected form of A (as the acid or amide) in any standard peptide method of synthesis. The starting material 7-arginine acids, such as those of formula I in which P is an arginine-like unit as defined above and A is hydroxy; are prepared as described above by a resin-supported or solution reaction sequence.

The end compounds of the invention have $V_1$ and/or $V_2$ vasopressin antagonist activity. Vasopressin is known to contribute to the anti-diuretic mechanism of action within the kidney. When the action of these compounds antagonizes that of the natural anti-diuretic hormone (ADH), the body excretes water due to an increased permeability of the terminal portions of the renal tubule. The mechanism of action is at the vasopressin receptors ($V_2$-receptors) located on the plasma membrane of certain renal epithelial cells. The most notable pharmacodynamic effect of the ADH antagonists of the invention is that of a water diuretic rather than of a natriuretic such as hydrochlorothiazide.

Any patient suffering from the syndrome of inappropriate antidiuretic hormone secretion (SIADH) or from an undesirable edematous condition is a target for the claimed compounds. Examples of clinical conditions indicated for the compounds of this invention include hypertension, hepatic cirrhosis, hyponatremia, congestive heart failure or a component of any traumatic condition resulting from serious injury or disease. The compounds of formula I in which $R_1$ and $R_2$ form a 5 or 6 membered ring are especially potent $V_2$-antagonists.

The second group of vasopressin receptor sites are the vascular pressor sites ($V_1$-receptors) within the cardiovascular system itself. These may also be antagonized by the compounds of this invention. The congeners of formula I in which $R_1$ and $R_2$ are hydrogen or methyl are potent $V_1$-antagonists. These compounds also have substantial anti-oxytocic activity.

The compounds of this invention, therefore, are used especially to induce anti-hypertensive, anti-oxytocic or diuretic activity in patients in need of such treatment. The latter comprises the administration internally, parenterally, buccally or by insufflation, of a nontoxic but effective quantity of the chosen compound, preferably dispersed in a pharmaceutical carrier. Dosage units of the active ingredient are selected from the range of 0.01 to 10 mg/kg, preferably 0.1 to 1 mg/kg, of base based on a 70 kg patient. The dosage units are administered to the human or animal patient from 1 to 5 times daily.

The pharmaceutical composition, which contains an active antagonist ingredient of formula I, comprises a dosage unit which is dissolved or suspended in a standard liquid carrier, such as isotonic saline, and is contained in an ampoule or a multiple dose vial suitable for a parenteral injection such as for intravenous, subcutaneous or intramuscular administration. A composition for insufflation may be similar but is usually administered in a metered dose applicator or inhaler. Pulverized powder compositions may, also, be used along with oily preparation, gels, buffers for isotonic preparations, buccal losenges, trans-dermal patches and emulsions or aerosols.

$V_2$-antagonistic activity toward the natural anti-diuretic hormone (anti-ADH activity) is determined, in vitro, in the medullary tissue of hog or human kidneys and, in vivo, in the hydropenic rat. The in vitro assay procedures for vasopressin stimulated adenylate cyclase activation or vasopressin binding activity are described by F. Stassen et al., J. Pharmacology and Experimental Therapeutics, 223, 50-54 (1982). $V_1$-antagonistic activity is determined by procedures using the rat thoracic aorta tissue and plasma membranes of rat liver. These procedures are described in the noted Stassen publication and in a publication at the 1st International Conference on Diuretics, Miami, Fla., March (1984). Oxytocin antagonism is determined as described by W. Sawyer et al., Endocrinology, 106 81 (1979).

The assay for anti-ADH activity in vivo is the hydropenic rat protocol described below:

HYDROPENIC RAT SCREEN

Food and water are removed from male rats approximately 18 hours prior to testing. Animals are housed 4 per metabolism cage. At 0 hour, the test compound is administered intraperitoneally to the test group and an equivalent volume of vehicle is administered to both control groups (fasted and non-fasted). Urine volume and osmolality are measured every hour for 4 hours. Test values are recorded as ml of urine excreted (cumulative), mEg/rat electrolyte excreted, mg/rat urea excreted, and osmolality in milli-Osmoles/Kg $H_2O$. A tolerance test is used to determine significance. $ED_{300}$ is defined as the dose of compound (μg/kg) required to lower urine osmolality to 300 m-Osmoles/kg.

TABLE 1

Pmp—D-Tyr(Et)—Phe—Val—Asn—Cys—X

|     | Kb (nM) | Ki (nM) | $ED_{300}$ (μg/kg) | (n) |
|---|---|---|---|---|
| (A) ArgArg(NH₂) | 2.7 | 2.0 | 7.2 | (2) |
| (B) Arg(NH₂) | 9.0 | 2.5 | 58 | (3) |
| (C) ProArg(NH₂) | 12 | 4.5 | 9.2 | (15) |
| (D) ArgGly(NH₂) | 17 | 2.7 | 22.7 | |
| (E) D-ArgArg(NH₂) | 2.7 | 1.9 | 14.6 | |
| (F) Arg—D-Arg(NH₂) | 5.4 | 1.7 | — | |
| (G) D-Arg—D-Arg(NH₂) | 5.2 | 0.88 | 13.5 | |

The compounds in Table 1 are a series of compounds which have the same ring members. Comparison is made between a species of this invention (A) and three earlier reported compounds (B, C and D). These data demonstrate compound A to be the most potent vasopressin antagonist yet reported in the desPro series of VSP-like compounds. In the in vivo rat, Compound A is 8 times more active than Compound B and 3 times more active than Compound D. "n" is the number of tests.

The following examples are intended to demonstrate the preparation and use of the compounds of this invention. All temperatures are in degrees Centigrade.

EXAMPLE 1

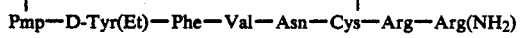

Pmp—D-Tyr(Et)—Phe—Val—Asn—Cys—Arg—Arg(NH₂)

The protected peptide intermediate resin, Pmp(4-MeBzl)-D-Tyr(Et)-Phe-Val-Asn-Cys(4-MeBzl)-Arg(Tos)-Arg(Tos)-BHA was synthesized by solid-phase methods on benzhydrylamine resin (BHA). On a shaker, 1.0 mmol of the BHA-resin was used. All amino acids were protected as tert.-butyloxycarbonyl (Boc) on the nitrogen and, then, coupled sequentially using DCC/HBT. The Pmp(4-MeBzl) was coupled using DMAP. The peptide was cleaved from the resin with deprotection of the side-chain protecting groups by using anhydrous HF (30 ml) in presence of anisole (3.0 ml) at 0° for 60 minutes. After evaporation in vacuo to dryness, the residue was washed with anhydrous ether. The crude peptide was extracted with dimethylformamide (100 ml) and 40% acetic acid (100 ml) into 3.5 liters of water which had been previously adjusted to pH 4.5. The aqueous-diluted disulfhydryl octapeptide mixture was oxidatively cyclized with 75 ml of 0.01M potassium ferricyanide at pH 7.2. The pH of the solution was adjusted to 4.5 using glacial acetic acid. It was passed through a weakly acid, acrylic resin (Bio-Rex 70) column. The column was eluted with pyridine-acetate buffer (30:4:66, pyridine/glacial acetic acid/water/v/v). The pyridine acetate was removed by distillation in vacuo. The residue was lyophilized from dilute acetic acid to give 284.19 mg of partially purified crude peptide.

Purification (1) Counter-current distribution (CCD): Sample: 284.19 mg, n-Butanol/Acetic Acid/Water (n-BuOH/HOAc/H₂O) 4:1:5; 240 transfers
  (a) fr. 116–144, 112.48 mg.
  (b) fr. 112–115 and 145–166, 34.42 mg.
(2) Gel-filtration: Sephadex G-15, 0.2M HOAc, used 112.48 mg from (1a) to obtain (2a), 19.28 mg; (2b) 50.08 mg and (2c) 7.99 mg.

Sample 2a purity 96% was submitted for testing.

Physical Data

MF: $C_{52}H_{79}N_{15}O_{10}S_2$, M.Wt. 1137.543
FAB: (M+H)⁺1138; (M−H) 1136
AAA: Asp (1.00), Cys (0.51), Val (1.07), Tyr (0.78), Phe (0.95), Arg (2.17).
Peptide Content: 93.2%

Chromatography Data

1. Thin layer Chromatography (TLC)

(a)

n-Butanol/Acetic Acid/Water/Ethyl Acetate (B/A/W/E) (1:1:1:1:), $R_f$ 0.5
n-Butanol/Acetic Acid/Water/Pyridine (B/A/W/P) (15:3:3:10), $R_f$ 0.6

2. High Pressure liquid Chromatography (HPLC), Altex ultrasphere ODS column, 5μ, 4.5 mm×25 cm
a 0.1% TFA/b CH₃CN (a)

Gradient 75 a: 25b to 45:55
k'=11.46

(b)

Isocratic 60 a/40 b
k'=4.85

EXAMPLE 2

Pmp—D-Tyr(Et)—Phe—Val—Asn—Cys—D-Arg—Arg(NH₂)

The protected peptide intermediate resin, Pmp(4-MeBzl)-D-Tyr(Et)-Phe-Val-Asn-Cys(4-MeBzl)-D-Arg(Tos)-Arg(Tos)-BHA was synthesized on 1.0 mmol benzhydrylamine resin as in Example 1. The HF cleavage was carried out and the oxidation with 0.01M potassium ferricyanide was performed as in Example 1 to give 371.09 mg (35.2%) of partially purified peptide.

Purification (1) Counter-current distribution: Sample 371 mg, n-BuOH/HOAc/H₂O, 4:1:5, v/v 240 transfers,
  (a) fr. 143–159; 105.59 mg
  (b) fr. 124–134 and 160–170; 64.3 mg
  (c) fr. 135–142; 36.22 mg (2) 105.59 mg from (1a) was redissolved in 1% acetic acid and filtered through a milipore filter (0.45μ). The filtrate was lyophilized to give 51.06 mg.

(3) HPLC repreparation: Sample 25 mg from (2), Altex ODS, 10 mm×25 cm, 5μ flow rate 5 ml/min, 0.1% Trifluoroacetic acid (TFA): Acetonitrile (CH₃CN) (60:40), isocratic, 229 nm (2.0 AUFS), to give 15.37 mg of sample 96-97% pure.

Physical Data

M.F. $C_{52}H_{79}N_{15}O_{10}S_2$, M.Wt. 1137.543.
FAB: $(M+H)^+ 1138$, $(M-H)^- 1136$
AAA: Asp (1.00), Cys (0.5), Val (1.05), Tyr (0.44), Phe (1.10), Arg (1.94).
Peptide Content: 59.91 ($N_2$ analysis).

Chromatography Data

1. TLC (a)

B/A/W/E (1:1:1:1 v/v); $R_f 0.525$
B/A/W/P/(15.3:3:10); $R_f 0.438$

2. HPLC, Altex ultrasphere ODS column, 5μ, 0.45 mm×25 cm.
   a 0.1% TFA/b CH₃CN a.

Gradient 80:20 to 50:50, K'=10.16 b.

Isocratic 55:45, K'=3.0
Isocratic 60:40, K'=5.67

EXAMPLE 3

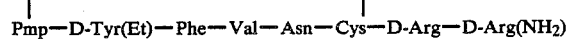
Pmp—D-Tyr(Et)—Phe—Val—Asn—Cys—D-Arg—D-Arg(NH₂)

The protected peptide intermediate resin, Pmp-(4-MeBzl)-D-Tyr(Et)-Phe-Val-Asn-Cys(4-MeBzl)-D-Arg(Tos)-D-Arg(Tos)-BHA was synthesized on 1.0 mmol of benzhydrylamine resin as in Example 1. The HF cleavage and oxidation with 0.01M potassium ferricyanide were performed similarly to give >1.0 g of oily material.

Purification (1) Counter-current distribution: The oil sample (crude from the Bio-Rex-70 column), BuOH/HOAc/H₂O, 4:1:5; 240 transfers.
  (a) fr. 114-154: 858 mg
  (b) fr. 155-200: 60 mg (2) Gel filtration, Sephadex G-15, 0.2M HOAc, sample 123 mg from 1a to obtain (2a) 74.40 mg, 2b 12.75 mg, 2c, 0.61 mg.

(3) HPLC repreparation: Sample 50 mg from 2b, Altex ODS, 10 mm×25 cm 5μ flow rate 5.0 ml/min, 0.1% TFA/CH₃CN (60:40) isocratic 229 nm (2.0 AUFS), to give 11.56 mg (6.5 mg 98%, 5.06 mg <98% pure).

Physical Data

M.F. $C_{52}H_{79}N_{15}O_{10}S_2$, M.Wt. 1137.543
FAB: $(M+H)^+ 1138$
AAA: Asp (1.00), Cys (0.49), Val (1.01), Tyr (0.30), Phe (1.04), Arg (1.76).
Peptide Content: 63.4%

Chromatography Data

1. TLC
  (a) B/A/W/E (1:1:1:1), $R_f 0.46$
  (b) B/A/W/P (15:3:3:10), $R_f 0.393$
2. HPLC, a 0.1% TFA; b CH₃CN
  a Gradient 80:20 to 50:50; k'=7.83
  e,uns/b/ Isocratic 55:45; k'=2.63

EXAMPLE 4

Pmp—D-Tyr(Et)—Phe—Val—Asn—Cys—Arg—D-Arg(NH₂)

The protected peptide intermediate resin, Pmp(4-MeBzl)-D-Tyr(Et)-Phe-Val-Asn-Cys(4-MeBzl)-Arg(Tos)-D-Arg(Tos)-BHA was synthesized on 1.0 mmol benzhydrylamine resin as in Example 1. The HF cleavage and oxidation with 0.01M potassium ferricyanide were performed as in Example 1 to give 252.46 mg of peptide.

Purification (1) Counter-current distribution: The sample 252.46 mg (crude), BuOH/HOAc/H₂O, 4:1:5; 240 transfers,
  (a) fr. 82-102: 111.47 mg
  (b) fr. 76-81 and 103-152: 65-87 mg (2) Gel-filtration: Sephadex G-15, 0.2M HOAc, sample 114.47 mg from 1a to obtain (2a): 39.85 mg, (2b): 29.83 mg. Fraction (2a) was tested for biological activity as 98% pure.

Physical Data

M.F. $C_{52}H_{79}N_{15}O_{10}S_2$, M.Wt. 1137.543.
FAB: $(M+H)^+ 1138$, $(M-H)^- 1136$.
AAA: Asp (1.00), Cys (0.56), Val (0.90), Tyr (0.55), Phe (0.93), Arg (1.87).
Peptide Content: 80.4%; 85.16% ($N_2$ analysis).

Chromatography Data

1. TLC
  a B/A/W/E (1:1:1:1), $R_f 0.57$
  b B/A/W/P (15:3:3:10), $R_f 0.39$
2. HPLC
  a 0.1% TFA/b CH₃CN
  1. Gradient 80 a: 20 b to 50:50; k'=9.59
  2. Isocratic 55 a: 45 b, k'=3.05

EXAMPLE 5

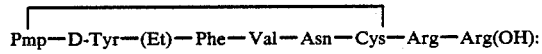
Pmp—D-Tyr—(Et)—Phe—Val—Asn—Cys—Arg—Arg(OH):

The protected peptide intermediate used, Pmp(4-MeBzl)-D-Tyr(Et)-Phe-Val-Asn-Cys(4-MeBzl)-Arg-(Tos)-Arg(Tos)-OCH₂C₆H₄-Resin was synthesized on 1.0 mmol of Boc-Arg(Tos)-O-Bzl-Resin (purchased from Peninsula Laboratories). The HF cleavage and oxidation with 0.01M ferricyanide were peformed as described above. The dilute solution was purified through a reversed phase silica gel C-18 column, and the peptide was eluted with 50% aqueous CH₃CN containing 0.1% TFA to give 549.62 mg (46.7%) of peptide.

Purification (1) Partition column chromatography G-25 sephadex. Sample 120 mg, nBuOH/HOAc/H₂O, 4:1:5; v/v.
  a 56.0 mg
  b 20.68 mg (2) HPLC: 25 mg from 2 a, Altex ODS, 10 mm×25 cm, 5μ flow rate 5.00 ml/min, 0.1% TFA: CH₃CN (58:42) isocratic 229 nm (2.0 AUFS) to give 10.65 (6.16, 96.5%, 4.49 mg <96%).

Physical Data

M.F. $C_{52}H_{78}N_{14}O_{11}S_2$, M.Wt. 1138.527
FAB: (M+H)⁺1139; (M−H)⁻1137
AAA: Asp (1.07); Cys (0.53); Val (0.97); Tyr (0.3); Phe (0.92); Arg (1.71)
Peptide Content: 79.8%.

Chromatography Data

1. TLC
   a B/A/W/E (1:1:1:1), R$_f$0.53
   b B/A/W/P (15:3:3:10), R$_f$0.25
2. HPLC
   a 0.1% TFA/b CH₃CN
   1. Gradient 80 a: 20 b to 50:50 K=8.0
   2. Isocratic 58 a: 42 b: K′=4.27

EXAMPLE 6

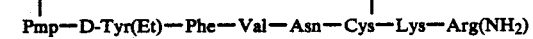

Pmp—D-Tyr(Et)—Phe—Val—Asn—Cys—Lys—Arg(NH₂)

The protected peptide intermediate resin, Pmp-(4-MeBzl)-D-Tyr(Et)-Phe-Val-Asn-Cys(4-MeBzl)-Lys(ClZ)-Arg(Tos)-BHA was synthesized on 1.0 mmol of benzhydrylamine resin as above. The HF cleavage and oxidation with 0.01M ferricyanide were performed as described to give 710.17 mg of partially purified peptide.

Purification (1) CCD, Sample 710.17 mg; (B/A/W, 4:1:5 v/v), 240 transfers
  (a) 106–130, 327.19 mg
  (b) 131–156, 100.1 mg
  (c) 64–100, 61.95 mg
  (d) 50–63+157–180, 41.38 mg (2) Gel filtration: Sephadex G-15, 0.2M HOAc, sample 100 mg from 1 a
  (2a) 70.21 mg
  (2b) 22.98 mg
Fraction 2a was 98–99% pure.

Physical Data

M.F. $C_{52}H_{79}N_{13}O_{10}S_2$, M.Wt. 1109.53
FAB: (M+H)⁺1110, (M−H)⁻1108

Chromatography Data

1. TLC
   (a) B/A/W/E, 1:1:1:1 v/v, R$_f$0.5
   (b) B/A/W/P, 15:3:3:10 v/v, R$_f$0.19
   (c) B/A/W, 4:1:5 upper v/v, R$_f$0.27
2. HPLC
   1. Gradient 80:20 to 50:50 of 0.1% TFA/CH₃CN, k′=11.32
   2. Isocratic 60:40 of 0.1% TFA/CH₃CN, k′=6.6

EXAMPLE 7

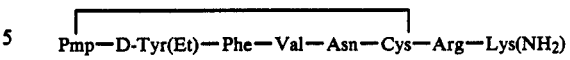

Pmp—D-Tyr(Et)—Phe—Val—Asn—Cys—Arg—Lys(NH₂)

The protected peptide intermediate resin, Pmp-(4-MeBzl)-D-Tyr(Et)-Phe-Val-Asn-Cys(4-MeBzl)-Arg(Tos)-Lys(ClZ)-BHA, was synthesized on 1.0 mmol of benzhydrylamine resin. The HF cleavage and oxidation with 0.01M ferricyanide were performed similarly to give 702.5 mg.

Purification (1) CCD, Sample 702.5 mg (B/A/W, 4:1:5 v/v), 240 transfers
  (a) 101–144, 468.82 mg
  (b) 96–100+145–160, 36.19 mg
  (c) 55–95, 55.19 mg (2) Gel filtration: Sephadex G-15, 0.2M HOAc, sample 100 mg of 1 a
  (2a) 67.27 mg
  (2b) 30.2 mg
2a was 96–97% pure.

Chromatography Data

1. TLC
   a B/A/W/E, 1:1:1:1 v/v, R$_f$0.54
   b B/W/A/P, 15:3:3:10 v/v, R$_f$0.42
2. HPLC
   1. Gradient 80:20 to 50:50 of 0.1% TFA/CH₃CN, k′=12.11
   2. Isocratic 55:45 of 0.1% TFA/CH₃CN, k′=3.69

EXAMPLE 8

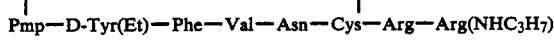

Pmp—D-Tyr(Et)—Phe—Val—Asn—Cys—Arg—Arg(NHC₃H₇)

A mixture of 0.1 mmol of the acid terminal peptide prepared as in Example 5 and 0.1 mmol of n-propylamine in 20 ml of dimethylformamide is reacted with 23 mg (0.11 mmol) of DCC and 14 mg (0.11 mmol) of HBT at room temperature for four hours. The volatiles are evaporated to give a product residue which is purified as described above.

EXAMPLE 9

Preparation Using Fragmentation Coupling

A. Preparation of

Pmp—D-Tyr(Et)—Phe—Val—Asn—Cys—Arg(OH)

The protected peptide intermediate resin, i.e., Pmp(4-MeBzl)-D-Tyr(Et)-Phe-Val-Asn-Cys(4-MeBzl)-Arg(Tos)-OCH₂-C₆H₄-Resin was synthesized manually on a shaker. Boc-Arg(Tos)-OCH₂C₆H₄-Resin was obtained from a commercial source with substitution of 0.35 meq./g. The protected peptide-resin intermediate was synthesized step-wise by deprotecting the Boc-group using 1:1 TFA:CH₂Cl₂ and coupling with the following amino acids using DCC/HBT to activate and catalyze coupling on 1.0 mmol to give 3.15 g of Pmp(4MeBzl)-D-Tyr(Et)-Phe-Val-Asn-Cys(4-MeBzl)-Arg(Tos)-OCH₂-C₆H₄-Resin. The titled peptide was obtained by cleavage from the resin and, deprotection of the side chain protecting group using HF 30 ml in the presence of 3.0 ml of anisole at 0° for 60 minutes. After evaporation in vacuo to dryness, the residue therefrom was washed with anhydrous diethyl ether. The peptide was extracted with degassed dimethylformamide, 1N ammonium hydroxide, then 40% acetic acid into a deaerated 3.5 l of water. The aqueous diluted disulfhydryl heptapeptide was oxidatively cyclized using 60 ml of 0.01M potassium ferricyanide at pH 7.2 until color persisted for 30 minutes. After completion of the oxidation reaction, the pH was adjusted to 4.5 using glacial acetic acid. This solution was filtered and the filtrate was flashed through a C-18 silica chromatography procedure. The peptide was eluted with 1:1 0.1% TFA/CH$_3$CN to give 245 mg (25%) of the intermediate peptide in three fractions, about 90% pure.

Purification

A sample 22.0 mg of the purest fraction was submitted to high performance liquid chromatography using Altex ODS, 10 mm×25 cm, 5μ, flow rate 5 ml/mn, 0.1% TFA/CH$_3$CN (60:40) isocratic, 220 nm (0.5 AVIS), 10.10 mg.

Physical Data

M.F. C$_{46}$H$_{66}$N$_{10}$O$_{10}$S$_2$,
M.Wt. 982.5
FAB: (M+H)$^+$983 and (M−H)$^-$981
AAA: Asp (1.00), Cys (0.27), Val (0.95), Tyr (0.50), Phe (0.99), Arg (1.07)
Peptide Content: 74.93%

Chromatography Data

1. TLC
   a B/A/W/E (1:1:1:1), R$_f$=0.6
   b B/A/W (4:1:5 upper), R$_f$=0.3
2. HPLC
   (a) Gradient k'=14.6
   (b) Isocratic k'=5.97

B. Preparation of Pmp—D-Tyr(Et)—Phe—Val—Asn—Cys(OH)

4.87 G (15 mmol) of the BocCys(4MeBzl) was dissolved in 30 ml of ethanol and 10 ml of water added. The pH was then adjusted to 7.1 with an aqueous solution of cesium bicarbonate.

The mixture was concentrated and the residue evaporated three times from 50 ml of toluene. This residue was, then, placed under high vacuum at ambient temperature overnight.

The salt was dissolved in 35 ml of dimethylformamide and 5 g of commercial chloromethylphenyl resin added. The mixture was stirred at 53° under argon overnight.

The mixture was filtered and the resin washed with dimethylformamide (5×60 ml), DMF/Water, 9:1, (5×60 ml), DMF (5×60 ml) and ethanol (6×60 ml). It was, then, dried under high vaccuum at ambient temperature over the weekend.

The peptide chain was built up on a 0.5 mmol Boc-Cys(4MeBzl)-Resin in a Beckman synthesizer as described above using the Boc derivatives of Asn, Val, Phe, D-Tyr(Et) and the S-(4-MeBzl) Pmp derivative. The resin was removed, washed and dried in vacuo.

0.86 G of the peptide resin was treated with 1.5 ml of anisole and stirred for 60 minutes at 0° in 15 ml of hydrogen fluoride. The hydrogen fluoride was, then, removed under aspirator pressure at 0°.

The residue was then washed with 3×25 ml of ether (discarded) and the peptide eluted with dimethylformamide and 30% acetic acid (4×10 ml). This solution was added to 2 l of degassed water and the pH adjusted to 7.0 with ammonium hydroxide. A 0.01M potassium ferricyanide solution was added slowly (35 ml).

The pH was then adjusted to 4.5 with acetic acid and the mixture stirred for 30 minutes with 25 g (wet) of a weakly basic ion exchange resin (ag-3×4 Ir-4S). The suspension was filtered and the resin washed with 2×400 ml of 30% acetic acid.

The filtrate was, then, passed through a C$_{18}$ flash column (7×16 mm). The column was then washed with water (3×400 ml) and the peptide eluted with acetonitrile/water/TFA, 50:50:0.25. Fractions 30–36 were combined, concentrated and lyophilized to yield 80 mg of the titled free Cys(OH) cyclic intermediate.

FAB mass spectrum in glycerol: 827 (M+H)$^+$, 825 (M−H)$^-$.

C. Condensation

The 6-Cys acid (20 mg) from B above is reacted with one equivalent of Arg-Arg(NH$_2$). 3HCl in the presence of DCC. HBT and one equivalent of triethylamine in dimethylformamide to produce the compound of Example 1. Similarly, 7-Arg acid from A is reacted with Arg(2HCl) (OMe) to give the acid parent of the compound of Example 5 after mild hydrolysis of the ester. This compound is isolated as the potassium salt if desired. One equivalent of Arg(NH$_2$) 2HCl is coupled with the 7-Arg acid from A using DCC/HBT to give the desired product.

EXAMPLE 10

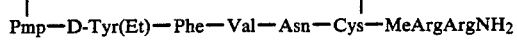

Pmp—D-Tyr(Et)—Phe—Val—Asn—Cys—MeArgArgNH$_2$

The protected peptide intermediate resin, Pmp-(4-MeBzl)-D-Tyr(Et)-Phe-Val-Asn-Cys(4-MeBzl)-N-MeArg-(Tos)-Arg(Tos)-BHA was prepared by the solid-phase method on benzhydrylamine resin. On a shaker, 0.5 mmol of BHA resin was used,all amino acids were protected as tert.-butyloxycarbonyl on the nitrogen and coupled sequentially using DCC/HBT. Boc-N-CH$_3$Arf(Tos) was prepared. Pmp(4-MeBzl) was coupled using DMAP. The peptide was cleaved from the resin with deprotection of the sidechain protecting groups using anhydrous HF (20 ml) and anisole (2 ml) at 0° for 60 minutes. After evaporation in vacuo to dryness, the residue was washed with anhydrous diethyl ether. The crude peptide was extracted with degassed 50% acetic acid (100 ml) and degassed DMF (60 ml) into a 2 l degassed water, at pH 4.5 The aqueous diluted disulfhydrylloctapeptide was oxidatively cyclized with 50 ml of 0.01M ferricyanide at pH of the solution was adjusted to 4.5 using glacial acetic acid. It was purified over a weakly acid ion-exchange column (Bio-Rex 70) to give 375 mg of the partially purified peptide.

Purification

CCD, 375 mg in B/A/W, 4:1:5 v/v, 240 transfers to give;
   a 122–146, 106.42 mg
   b 147–156+110–121, 131.86 mg c 157-200+100-109, 32.80 mg Sample a 97-98% pure was submitted for biological evaluation.

Chromatography Data

1. TLC
   a B/A/W/E, 1:1:1:1. v.v, $R_f=0.68$
   b B/A/W, 4:1:5, v/v, upper $R_f=0.39$
2. HPLC
   a Gradient 80:20 to 50:50 0.1% TFA/CH$_3$CN, k'=11.93
   b Isocratic 55:45 0.1% TFA/CH$_3$CN, K'=4.29.

EXAMPLE 11

Substituting a stoichiometric quantity of Boc-L-Tyr(Et) for Boc-D-Tyr(Et) at the 2 unit of the peptide synthesis of Example 1 gives cyclized Pmp-L-Tyr(Et)-Phe-Val-Asn-Cys-Arg-Arg(NH$_2$).

Substituting in Example 1, Boc-D-Ile for Boc-D-Tyr(Et) at the unit gives Pmp-D-Ile-Phe-Val-Asn-Cys-Arg-Arg(NH$_2$).

Substituting Boc-L-Phe(4-Me) for the amino acid at the 3 unit and Boc-Nle at the 4 unit in the synthesizer sequence reactions of Example 1 gives Pmp-D-Tyr(Et)-Phe-(4-Me)-Nle-Asn-Cys-Arg-Arg(NH$_2$).

Substituting Boc-Cha at the 4 unit gives Pmp-D-Tyr-(Et)-Phe-Cha-Asn-Cys-Arg-Arg(NH$_2$).

Substituting unprotected Gln at position 4 using HBT gives Pmp-D-Tyr-(Et)-Phe-Gln-Asn-Cys-Arg-Arg(NH$_2$).

Substituting Boc-D-Pba at the 2 unit and Boc-Chg at the 4 unit of the detailed reaction sequence of Example 1 gives Pmp-D-Pba-Phe-Chg-Asn-Cys-Arg-Arg(NH$_2$).

EXAMPLE 12

Substituting the appropriate protected ring units in the above synthetic sequence gives the respective octapeptide or a salt thereof as follows:

a. [1-desaminopenicillamine-2-(O-ethyl)-D-tyrosine-3-(4'-methylphenylalanine)-7-arginine-8-arginine-9-desglycine]-vasopressin acetate;
b. [1-($\beta$-mercaptopropionic acid)-2-(O-ethyl)-D-tyrosine-4-($\alpha$-aminobutyric acid)-7-arginine-8-arginine-9-desglycine]-vasopressin;
c. [1-($\beta$-mercaptopropionic acid)-2-valine-4-cyclohexylglycine-7-arginine-8-arginine-9-desglycine]-vasopressin hydrochloride
d. [1-($\beta$-mercaptopropionic acid)-4-glutamine-7-arginine-8-homoarginine-9-desglycine]-vasopressin;
e. [1-desaminopenicillamine-2-phenylalanine-7-homoarginine-8-homoarginine-9-desglycine]-vasopressin;
f. [1-desaminopenicillamine-2-D-$\alpha$-aminophenylbutyric acid-4-isoleucine-7-L-arginine-8L-arginine-9-desglycinamide]-vasopressin.
g. [1-desaminopenicillamine-2-tryptophan-4-glutamine-7-D-arginine-8-D-arginine-9-desglycine]-vasopressin;
h. [1-($\beta$-mercapto-$\beta$,$\beta$-cyclopentamethylenepropionic acid)-2-L-tyrosine-3-(4'-methylphenylalanine)-7-araginine-8-arginine-9-desglycine]-vasopressin;
i. [1-($\beta$-mercaptopropionic acid)-2-(O-ethyl)-D-tyrosine-3-isoleucine-4-threonine-7-arginine-8-arginine-9-desglycine]-vasopressin acetate.

EXAMPLE 13

Parenteral Dosage Unit Compositions

A preparation which contains 0.10 mg of the peptide of Example 1 as a sterile dry powder for parenteral injection is prepared as follows: 0.5 mg of peptide is dissolved in 1 ml of an aqueous solution of 20 mg of mannitol. The solution is filtered under sterile conditions into a 2 ml ampoule and lyophilized. The reconstituted solution is administered to a patient in need of vasopressin antagonist treatment as necessary, from 1-5 times daily by injection or in an equivalent continous i.v. drip injection.

Nasal Dosage Unit Compositions 2.5 Mg of a finely ground peptide of this invention, such as the product of Example 2, is suspended in a mixture of 75 mg of benzyl alcohol and 1.395 g of a suspending agent such as a commercial mixture of semisynthetic glycerides of higher fatty acids. The suspension is placed in an aerosol 10 ml container which is closed with a metering valve and charged with aerosol propellants. The contents comprise 100 unit doses which are administered intranasally to a subject in need thereof from 1-6 times a day.

What is claimed is:

1. A compound having the formula:

$$R_1 \diagdown \underset{R_2 \diagup}{\overset{CH_2CO-X-Z-Y-Asn-Cys-P-A-B}{C}} \underset{S\text{———————}S}{|}$$

in which:

P is a D or L isomer of Arg, Lys, HArg, MeArg, MeLys or MeHArg;

A is a D or L isomer of Arg, Lys, HArg, MeArg, MeLys or MeHArg;

B is OH, NH$_2$ or NHAlk;

Z is Phe, Phe(4'-Alk), Tyr(Alk), Ile or Tyr; X is a D or L isomer of Phe, Phe(4'-AlK), Val, Nva, Leu, Ile, Pba, Nle, Cha, Abu, Met, Chg, Tyr or Tyr(Alk);

Y is Val, Ile, Abu, Ala, Chg, Gln, Lys, Cha, Thr, Nle, Phe, Leu or Gly; and

R$_1$ and R$_2$ are, each, hydrogen, methyl or, when taken together and with the $\beta$-carbon to which they are attached, a cycloalkylene ring of 4-6 members; and Alk is C$_{1-4}$-alkyl;

or a pharmaceutically acceptable salt or prodrug thereof.

2. A compound according to claim 1 in which R$_1$ and R$_2$, taken together, form a spiropentamethylene ring.

3. A compound according to claim 1 in which P-A-B is Arg-Arg(NH$_2$).

4. The compound of claim 1 in which the compound is [1-($\beta$-mercapto-$\beta$,$\beta$-cyclopentamethylenepropionic acid)-2-(O-ethyl)-D-tyrosine-4-valine-7-arginine-8-arginine-9-desglycine]-vasopressin or a phamaceutically acceptable, acid addition salt thereof.

5. The compound of claim 1 in which the compound is [1-($\beta$-mecapto-$\beta$,$\beta$-cyclopentamethylenepropionic acid)-2-(O-ethyl)-D-tyrosine-4-valine-7-D-arginine-8-D-arginine-9-desglycine]-vasopressin or a pharmaceutically acceptable, acid addition salt thereof.

6. The compound of claim 1 in which the compound is [1-($\beta$-mercapto-$\beta$,$\beta$-cyclopentamethylenepropionic acid)-2-(O-methyl)-L-tyrosine-4-valine-7-arginine-8-D-arginine-9-desglycine]-vasopressin or a pharmaceutically acceptable, acid addition salt thereof.

7. The compound of claim 1 in which the compound is [1-($\beta$-mercaptopropionic acid)-2-(O-ethyl)-D-tyrosine-3-isoleucine-4-threonine-7-arginine-8-arginine-9- desglycine]-vasopressin or a pharmaceutically acceptable, acid addition salt thereof.

8. The compound of claim 1 in which the compound is [1-(β-mercapto-β,β-cyclopentamethylenepropionic acid)-2-(O-ethyl)-D-tyrosine-4-valine-7-arginine-8-arginine-9-desglycinamide]-vasopressin or a pharmaceutically acceptable, acid addition salt thereof.

9. The compound of claim 1 in which the compound is 1-(β-mercapto-β,β-cyclopentamethylenepropionic acid-2-(O-ethyl)-D-tyrosine-4-valine-8-arginine-7-lysine-9-desglycine]-vasopressin or a pharmaceutically acceptable, acid addition salt thereof.

10. The compound of claim 1 in which the compound is [1-(β-mercaptopropionic acid)-2-(O-ethyl)-D-tyrosine-4-valine-7-N-methylarginine-8-arginine-9-desglycine]-vasopressin or a pharmaceutically acceptable, acid addition salt thereof.

11. A pharmaceutical composition having vasopressin antagonist activity comprising a pharmaceutical carrier and, dispersed therein, an effective therefor but nontoxic quantity of a compound of claim 1.

12. A pharmaceutical composition having vasopressin antagonist activity comprising a pharmaceutical carrier and, dispersed therein, an effective therefor but nontoxic quantity of the compound of claim 3.

13. A pharmaceutical composition having vasopressin antagonist activity comprising a pharmaceutical carrier and, dispersed therein, an effective therefor but nontoxic quantity of the compound of claim 4.

14. The method of producing vasopressin antagonist activity in a patient in need thereof which comprises administering parenterally or intranasally to said patient an effective thereof, nontoxic quantity of a compound of claim 1.

15. The method of producing vasopressin antagonist activity in a patient in need thereof which comprises administering parenterally or intranasally to said patient an effective therefor, nontoxic quantity of the compound of claim 3.

16. The method of producing vasopressin antagonist activity in a patient in need thereof which comprises administering parenterally or intranasally to said patient an effective therefor, nontoxic quantity of the compound of claim 4.

* * * * *